United States Patent [19]
Dawson et al.

[11] Patent Number: 5,341,690
[45] Date of Patent: Aug. 30, 1994

[54] COMPOSITE WASTEWATER SAMPLER

[75] Inventors: Brian D. Dawson; Richard D. Hartz, both of Lincoln, Nebr.

[73] Assignee: Isco, Inc., Lincoln, Nebr.

[21] Appl. No.: 421,559

[22] Filed: Oct. 13, 1989

[51] Int. Cl.$^5$ .......................... G01N 1/14; G01N 1/20
[52] U.S. Cl. .................. 73/863.61; 73/863.02; 73/863.83
[58] Field of Search ........... 73/863.61, 863.02, 863.03, 73/864.34, 864.35, 864.73, 864.74, 863.43, 863.52, 863.58, 863.83, 863.84, 863.81

[56] References Cited

U.S. PATENT DOCUMENTS

| | | | |
|---|---|---|---|
| 2,608,866 | 9/1952 | Breedlove et al. | 73/863.61 |
| 4,059,408 | 11/1977 | Boisde et al. | 73/864.23 X |
| 4,118,987 | 10/1978 | Zeh | 73/863.61 |

*Primary Examiner*—Tom Noland
*Attorney, Agent, or Firm*—Vincent L. Carney

[57] ABSTRACT

A composite wastewater sampler includes a flow-through-chamber having an inlet port and an outlet port with a path between them that gradually increases in depth and width and then decreases in width. It is shaped to cause fluid to (1) flow from the inlet port; (2) drop to a lower level of flow within the flow-through-chamber; (3) gradually adjust in cross-sectional shape to the outlet port; and (4) flow back into a wastewater pipe. A sampling nozzle extends into the flow-through-chamber adjacent to the inlet port and within the path of the downwardly flowing wastewater so that wastewater exiting the port contacts the nozzle and flows downwardly across it.

24 Claims, 8 Drawing Sheets

COMPOSITE WASTEWATER SAMPLER

BACKGROUND OF THE INVENTION

This invention relates to composite wastewater samplers.

In one type of composite wastewater sampler, samples are automatically periodically drawn from a wastewater pipe under the control of a computer and the samples are permitted to flow into a large container which accumulates the samples. The wastewater in the container is used to determine the content of flow over a period of time to learn of the amount of different solids and liquids in a wastewater system.

In one prior art wastewater sampler of this type, a peristaltic pump periodically draws samples directly from the pipe and flows it to a single container. A composite wastewater sampler of this type is sold under the designation model 2710FR Fiberglass Refridgerated Composite Wastewater Sampler by Isco, Inc., P.O. Box 82531, Lincoln, Nebr. 68501-2531, USA. This type of composite wastewater sampler has some disadvantages in that: (1) the nozzle which draw fluid from the pipe is easily clogged, and (2) if not carefully monitored by a human operator, the container may overflow.

Another prior art type of composite wastewater sampler includes a wastewater pipe which extends into a cabinet and has an outlet port opening into a flow-through-chamber which is larger than the waste-water pipe. Wastewater flows into the flow-through-chamber of a larger flow-bed area from which samples of wastewater are scooped up and permitted to flow into a container. After the wastewater flows through the flow-through-chamber, it is forced back into a return section of the pipe. A composite wastewater sampler of this type is sold under the designation model TC-2 Sampler by Sonford Samplers, a Division of Comelex Corporation, 905 North 5th Street, Minneapolis, Minn. 55401, USA.

This type of composite wastewater sampler has several disadvantages, such as: (1) it does not draw an accurate sample of the solids in the wastewater because the solids settle to a lower level before the scope receives them; (2) it is relatively complicated; and (3) it requires careful monitoring by human operators to be sure that containers gathering the composite sample do not overflow and are replaced timely.

SUMMARY OF THE INVENTION

Accordingly, it is an object of the invention to provide a novel composite wastewater sampler.

It is a further object of the invention to provide a novel method for drawing wastewater and storing it in a container.

It is a further object of the invention to provide a composite wastewater sampler that provides a better and more accurate indication of the content of wastewater.

It is a still further object of the invention to provide a wastewater sampler that automatically ends the sampling for one container and applies sampling to another container at a predetermined amount of fluid to prevent overflowing of a container even through the sampler is not attended by a human operator.

It is a still further object of the invention to provide a novel wastewater sampler which is not subject to clogging as prior art samplers.

According to the above and further objects of the invention, a composite wastewater sampler includes a flow-through-chamber having an inlet port and an outlet port with a path between them that gradually increases in depth and width and then decreases in width. It is shaped to cause fluid to: (1) flow from the inlet port; (2) drop to a lower level of flow within the flow-through-chamber; (3) gradually adjust in cross-sectional shape to the outlet port; and (4) flow back into a wastewater pipe. A sampling nozzle extends into the flow-through-chamber adjacent to the inlet port and within the path of the downwardly flowing wastewater so that wastewater exiting the port contacts the nozzle and flows downwardly across it.

Advantageously, the intake nozzle is located from between just outside the surface of the inlet port of the flow-through-chamber such as one-quarter inch to four inches from the inlet port in the direction of the flow-through-chamber depending on the expected velocity of the fluid. In the preferred embodiment, it is approximately three-quarters inch from the opening. The nozzle is tapered and smooth except for an aligning keyway. The taper is between 1½ to 3 degrees in slope with respect to a longitudinal axis inwardly toward the longitudinal axis opposite in direction to the flow of fluid and in the direction of the inlet port.

The intake nozzel: (1) is positioned at an angle to the vertical of between 5 and 40 degrees and preferably at an angle of 25 degrees from the vertical pointing in the direction of flow and normally at an angle that is at the same angle as the surface of the inlet port into the flow-through-chamber; (2) extends approximately to the middle of the flow stream from the inlet port but in its location is selected to provide substantial flow of fluid downwardly and to permit the tip to be in contact with the fluid for drawing fluid instead of air; and (3) has a bottom open end cut to provide an intake port facing the flow of the wastewater at an angle of 10 degrees with respect to the center line of the inlet port of the flow-through-chamber but may be at differing angles which are selected together with the angle with respect to the longitudinal axis of the nozzle and center axis of the inlet port to cancel venturi effect and permit drawing of fluid instead of air by a peristaltic pump at sampling intervals. The angle of the nozzel intake port may be between 5 and 40 degrees with respect to the longitudinal axis of the inlet port to the flow-through-chamber but in the preferred embodiment is 10 degrees.

A computer controlled peristaltic pump draws fluid at the same velocity as the fluid flowing through the wastewater pipe at preprogrammed intervals and deposits them into the sampling container. A computer counts revolutions of the peristaltic pump and the number of samples drawn and deposited into a container and from these measurements, it calculates the volume of samples in the container. Before the container is full, at a pre-programmed amount of liquid, the computer activates a motor which moves the outlet end of the peristaltic pump tubing over a second container to begin drawing samples and transferring them into the second container. With this arrangement, continuous human monitoring is not needed and yet overflowing of containers is avoided.

From the above description, it can be understood that the composite wastewater sampler of this invention has several advantages such as: (1) it is not easily clogged and is self-cleaning; (2) it takes a more representative and accurate sample of the amount of solids in the wastewater then the prior art wastewater samples; (3) it is relatively uncomplicated; (4) it is readily adaptable to scooping samples manually; (5) it permits automatic direct pumping for higher accuracy; and (6) it does not require continuous attendance and may fill sequentially composite containers automatically.

SUMMARY OF THE DRAWINGS

The above noted and other features of the invention will be better understood from the following detailed description when considered with reference to the accompanying drawings, in which.

DETAILED DESCRIPTION

Figure 1:
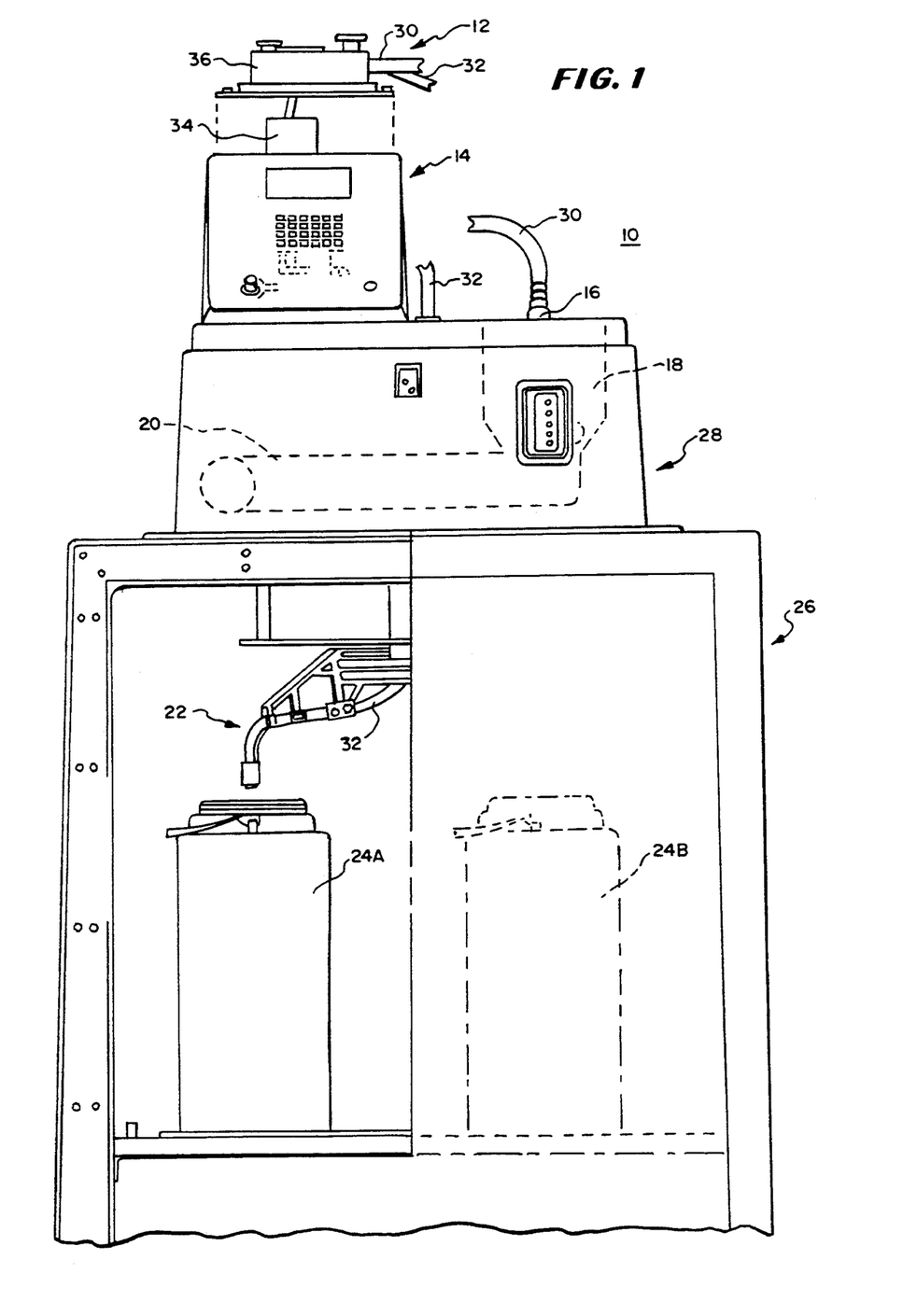
FIG. 1 is a fragmentary elevational view partly exploded of the composite wastewater sampler which is an embodiment of the invention.

In FIG. 1, there is shown a fragmentary elevational view, partly exploded, of a composite wastewater sampler 10 having a pump assembly 12, a computer 14, an intake nozzle 16, a flow-through-channel 18, a front horizontal portion 20 of the wastewater pipe and a distributor assembly 22. Wastewater flows through the wastewater pipe and through the flow-through-channel 18 in a continuous flow. During that flow, the computer 14 measures periods of time and activates the pump assembly 12 at preset intervals of time or wastewater flow to draw samples of predetermined amounts of wastewater.

During the drawing of a sample, the pump pumps at a predetermined rate set to be approximately the rate of flow of the wastewater through the front horizontal portion 20. During this pumping action, the pump pumps wastewater: (1) from the flow-through-channel 18; (2) through the intake nozzle 16 which is inserted into the flow-through-chamber 18; (3) through the hose sectors 30 and 32; and (4) to the distributor assembly 22 which deposits it in one of two sample composite containers 24A or 24B.

To provide pumping, the pump assembly 12 includes a peristaltic portion 36 having rollers which receive tubing, an inlet portion of which is indicated at 30 and an outlet portion of which is indicated at 32. The rollers are driven against a section of hose in a conventional manner by a motor 34 which is energized under the control of the computer 14 to cause power to be applied. The computer 14 counts revolutions of the peristaltic pump to monitor the purging of liquid from the tubing, and then pumping a fixed amount of sample into the composite container 24A through the hose sectors 30 and 32. This cycle is repeated to form a composite sample.

Figure 2:
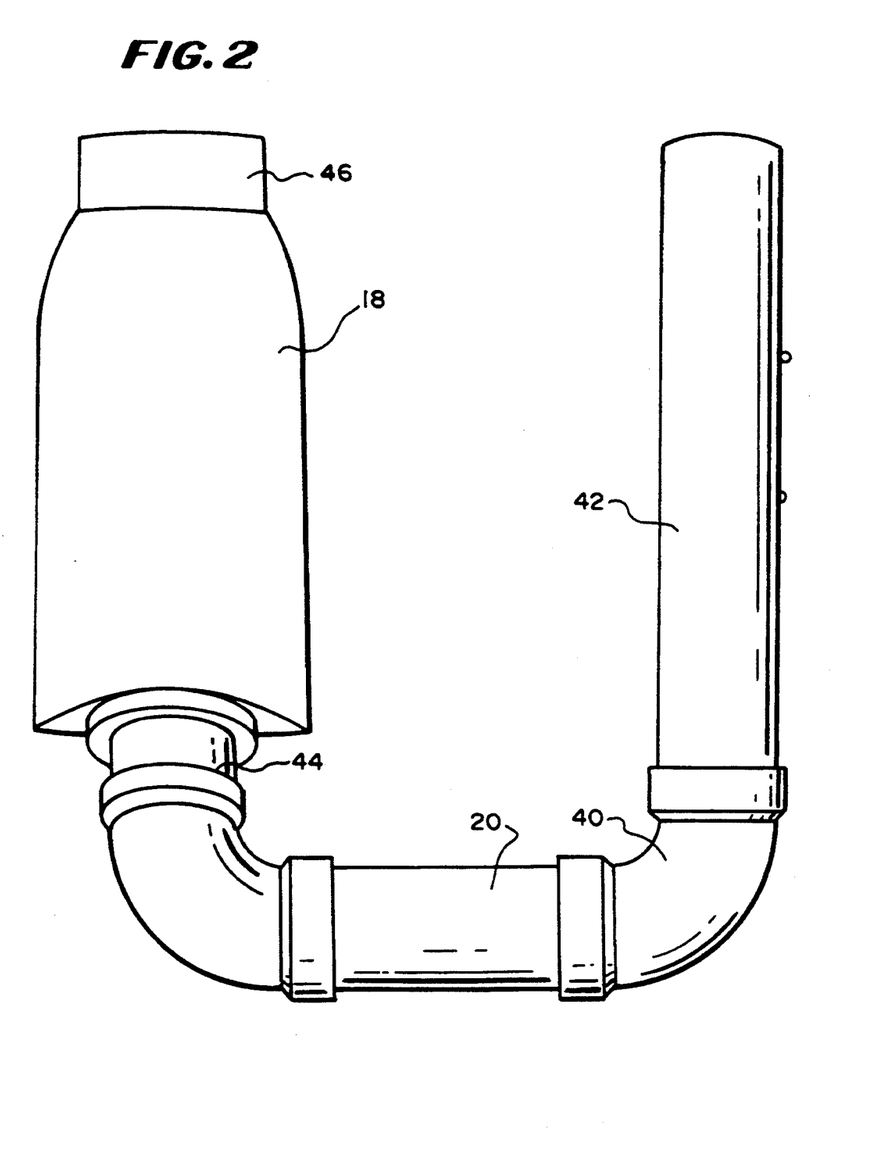
FIG. 2 is a bottom view of a portion of the wastewater sampler showing some pipes and a flow-through-chamber.

In FIG. 2, there is shown a bottom view of the flow-through-chamber 18 and front horizontal portion of the pipe 20 with the connecting pipe sections 40, 42, 44 and 46. As shown in this view, wastewater flows through the composite wastewater sampler 10 (FIG. 1) from a pipe 42, a connecting elbow 40, the front horizontal portion 20, a connecting upwardly angled pipe 44, the flow-through-chamber 18 and the connecting pipe section 46 in the named order. The water flows through these pipes at a linear velocity of between 1 foot per second and 12 feet per second and preferably at 1.8 feet per second. The rate of flow together with the angled curves maintains solid waste portions in suspension through the pipe sections and at least the entrance port of the flow-through-chamber 18.

Figure 3:
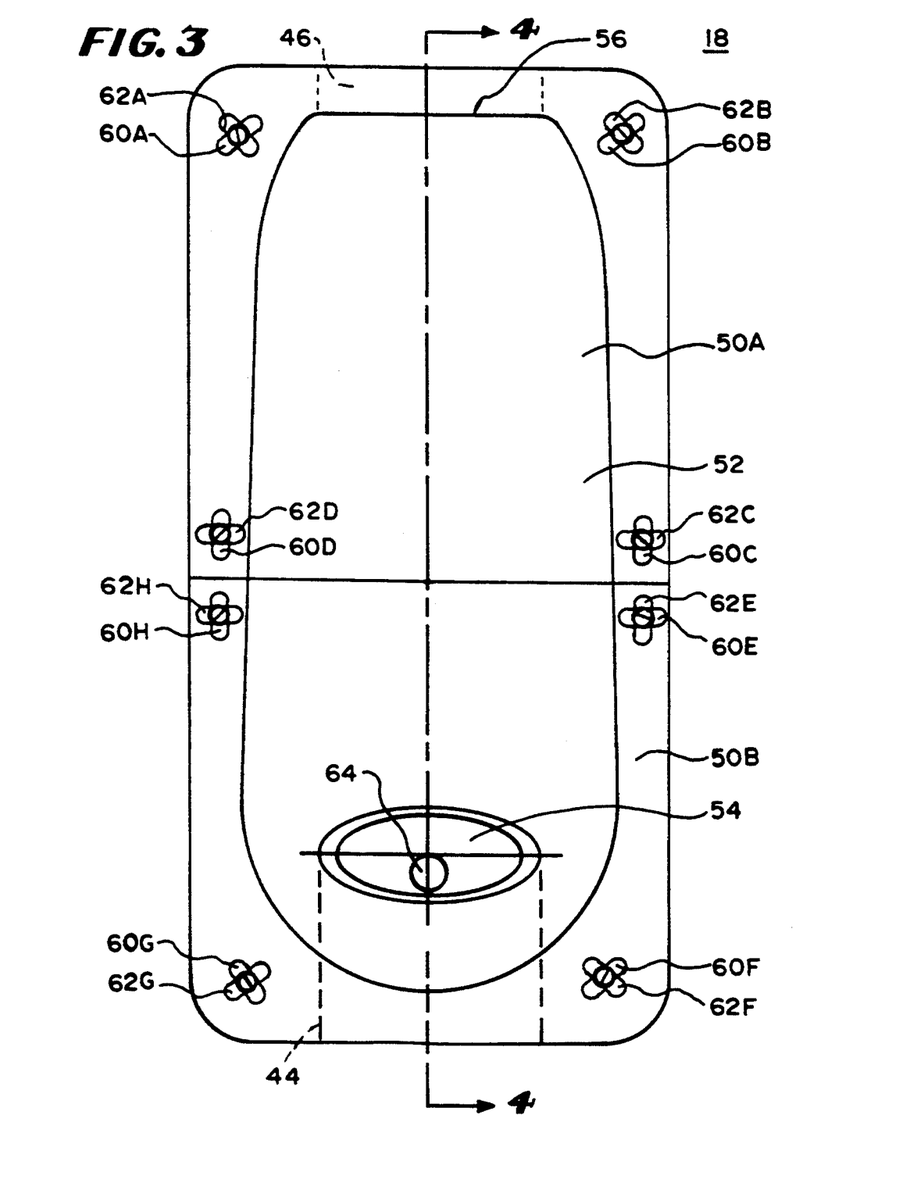
FIG. 3 is a plan view of the flow-through-chamber of FIG. 2.

In FIG. 3, there is shown a plan view of the flow-through-chamber 18 having a two-part cover 50A and 50B, shaped flow-bed walls 52 of the flow-through-chamber 18, an inlet port 54 and outlet port 56 as its principal parts. The cover parts 50A and 50B are transparent and removable to permit manual scooping of samples from the flow-through-chamber 18 and include a circular opening 64 through which the intake nozzle 16 (not shown in FIG. 3) may extend adjacent to the inlet port 54 for drawing samples of wastewater as it flows into the flow-through-chamber 18.

The flow-bed walls 52 of the flow-through-chamber 18 are shaped so that wastewater exiting the inlet port 54 drops to a lower wider level. The level of wastewater gradually changes to avoid turbulence between the inlet port 54 and outlet port 56. It drops as explained above and gradually reaches the level of the outlet port 56, at which time the cross section of the wastewater has a shape that channels the water smoothly without backup through the outlet port 56. For this purpose, the walls 52 drop steeply down from the inlet port 54 which extends into an inwardly slanted wall. Gradually the depth decreases and the width increases and then decreases as the distance from the inlet port increases up to the exit port to provide a smooth transition.

In the preferred embodiment, the inlet port 54 and outlet port 56 are spaced approximately 10 inches from each other and the inlet port 54 is circular on a slanted surface to appear elliptical in the view of FIG. 3, being at approximately a 65 degree angle with a horizontal and slanting inwardly toward the flow-through-chamber 18. It has a diameter of approximately 2.5 inches. However, these dimensions may vary with the principal criteria being to permit a flow over the intake nozzle 16 that is inserted through the aperture 64 in the cover.

To provide a transparent removable cover, the first section of the cover includes four elongated openings 60A, 60B, 60C and 60D through it and the second section includes a corresponding four openings, 60E, 60F, 60G and 60H. Eight elongated members 62A-62H extend into the walls of the flow-through-chamber 18 and are rotatably held spaced from the walls a distance equal to the thickness of the cover by screws. These elongated members may be rotated so they fit through the corresponding elongated openings 60A-60H or moved at an angle to them to hold the covers in place. Thus, by aligning the holding members with the slots, either side of the cover 50A and 50B can be removed.

Figure 4:
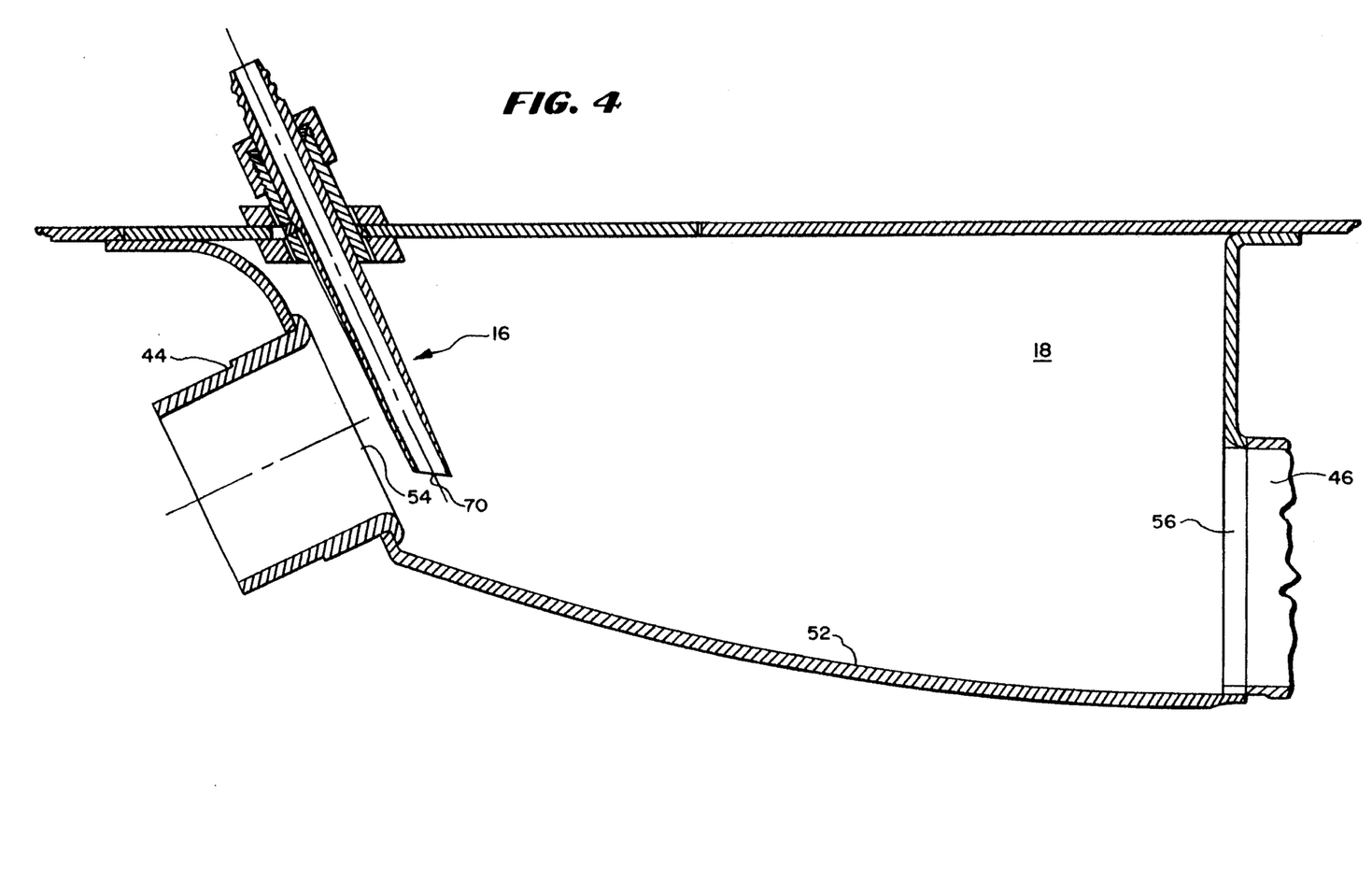
FIG. 4 is a sectional view taken through lines 4—4 of FIG. 3 illustrating the flow-through-chamber.

In FIG. 4, there is shown a sectional view of the flow-through-chamber 18 taken through lines 4—4 of FIG. 3 having a portion of the intake nozzle 16, the inlet port 54, the upwardly extending pipe member 44, the outlet port 56, and outlet pipe 46. As best shown in this view, the intake nozzle 16 tapers inwardly at angles of between 1½ and 3 degrees and preferably at an angle of approximately 2 degrees.

When mounted in place, the intake nozzle 16 is at an angle of approximately 25 degrees with the vertical but may be between 5 and 40 degrees. It is positioned sufficiently close to the inlet port 54 so that water flows across its tip. Depending on the velocity of the water, the tip of the intake nozzle 16 is anywhere from one-quarter inch away from the surface of the inlet port 54 to four inches from the surface of the inlet port 54 but is generally approximately three-quarters inch from the inlet port 54. The tip is cut upwardly to provide an intake port 70 having a portion facing into the flow of the water flowing through the inlet port 54. The angle of the intake port 70 is selected so that the pressure of the flowing wastewater cancels venturi forces and permits smooth uptake of liquid without air. Generally, the tip is some distance from the center line of the flow-through-chamber inlet port 54 but may be lower just so that the wastewater continually covers the inlet port 54 of the intake nozzle 16 during sample drawing. The angle of the inlet port 54 of the intake nozzle with the longitudinal axis of the intake nozzle 16 is approximately 30 degrees so that it is approximately 60 degrees from the perpendicular to the longitudinal axis of the intake nozzel 16.

Figure 5:
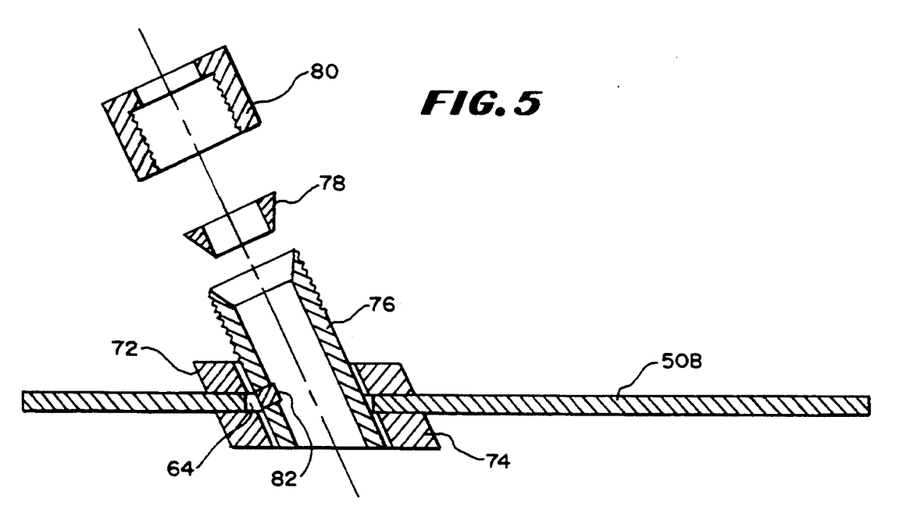
FIG. 5 is a fragmentary sectional view of a nozzle holder used in the embodiment of FIG. 1.

In FIG. 5, there is shown a holder for the intake nozzle 16 mounted in the plate 50B about the aperture 64 and includes first and second collars 72 and 74, a housing 76, a ferrule member 78 and an end member 80. The collars 72 and 74 are generally annular and shaped to receive a portion of the housing 76, with the collar 72 fitting above the plate 50B and the collar 74 below to form a seal about the housing 76.

The outer surface of the housing 76 has external threads to engage with internal threads on the inner surface of the end member 80 to receive the ferrule member 78 between them and compress it to hold the intake nozzle 16 in place and form a liquid tight seal thereabout. The housing 76 and upper and lower collars 72 and 74 are fastened in place about the aperture 64 with the end member 80 extending above the plate 50B. The housing 76 includes a key member 82 adapted to align the intake nozzle 16 in a manner to be described in connection with FIG. 6. With this arrangement, an installer can position the transparent covers over the flow-through-chamber with the collars 72 and 74 and housing 76 in place, slide the intake nozzle 16 into the housing 76 and position it with its inlet port 54 near the center of flowing wastewater, insert the ferrule member 78 and tighten the end member 80 to hold the intake nozzle 16 in place.

Figure 6:
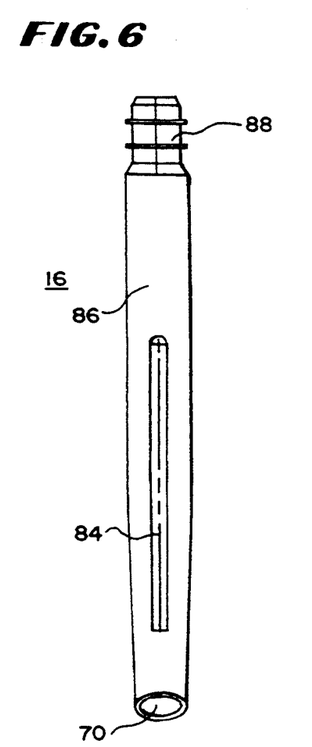
FIG. 6 is a rear elevational view of a nozzle used in the embodiment of FIG. 1.

In FIG. 6, there is shown an elevational view of an intake nozzle 16 having a tubular generally tapered cylindrical body 86, a keyway 84 sized to engage the key 82 (FIG. 5) for aligning the body 86 of the nozzle and a nipple 88. The nipple 88 receives the hose 30 (FIG. 1) of the peristaltic pump 12 (FIG. 1) to permit the drawing of fluid. The keyway 84 aligns the intake nozzle 16 so that the tip 70 faces the inlet port 54 (FIG. 4) to receive wastewater.

With this arrangement, wastewater continually flows downwardly over the tapered portion of the intake nozzle 16 in the direction of the taper, keeping it clear and free of clogging. When the pump assembly 12 draws a sample, the flow of fluid is pulled upwardly without air and turbulence partly because the flow of wastewater is at the same velocity as the pump is drawing and the intake part of the nozzle 16 is at an angle to receive the fluid in a manner that equalizes any venturi effect that might disrupt the intake. The intake linear velocity of the water in the tube 30 should be within 20 percent of the linear velocity of the wastewater in the wastewater pipes.

Figure 7:
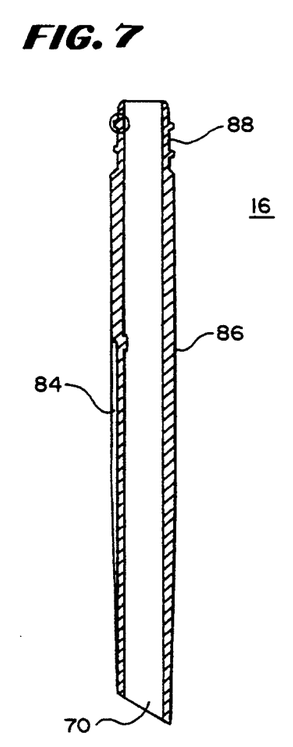
FIG. 7 is a sectional view of the nozzle of FIG. 6.

In FIG. 7, there is shown a sectional view of the intake nozzle 16 illustrating the taper on the wall 86 that prevents clogging of the tube by waste flowing in the wastewater stream and the keyway 84 that makes proper alignment convenient. The nozzle has an inside diameter of a size that provides a smooth transition between the intake hose of the pump assembly 12 and the intake nozzle 16.

In mounting the intake nozzle 16, the installer inserts the intake nozzel 16 and observes the flow of wastewater in the flow-through-chamber 18. The intake nozzle is manually adjusted by sliding it in its holder and the cover of the holder threades to lock the nozzle in place.

Figure 8:
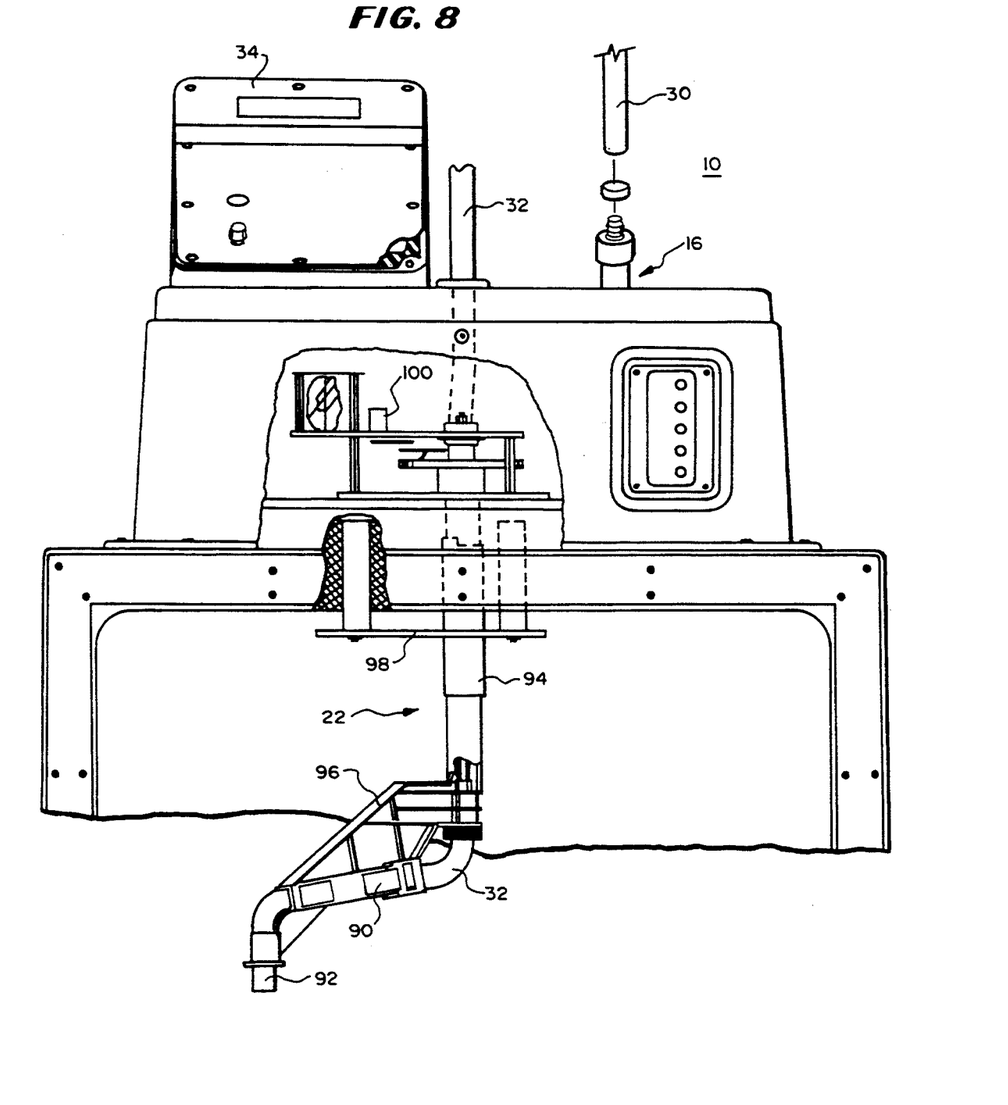
FIG. 8 is a fractional view partly broken away of an embodiment of a distributor of samples useful in the embodiment of FIG. 1.

In FIG. 8, there is shown a brown away, fragmentary elevational view of the composite flow through sampler 10 showing the manner in which the hose 32 from the pump assembly 12 extends downwardly from the pump assembly 12 (FIG. 1) to a distributor arm 96 of the distributor assembly 22. The distributor assembly arm 96 receives the hose 32 and supports it through an offset portion 90 and a downwardly extending portion 92 so that it extends outwardly from a central axis of rotation 94. The hose 32 is held in this position by the distributor arm 96 which rotates within a support section 98 under the control of a motor 100.

With this arrangement, the motor 100 when activated rotates the distributor arm 96 to move the downwardly extending portion 92 through 120 degrees from a position where it is over the container 24A to a position where it is over the container 24B. This is done under the control of the computer 14 so that, when a predetermined number of samples have been drawn, the arm is rotated to avoid overflowing of one of the containers 24A and 24B and to collect samples in the next container.

Figure 9:
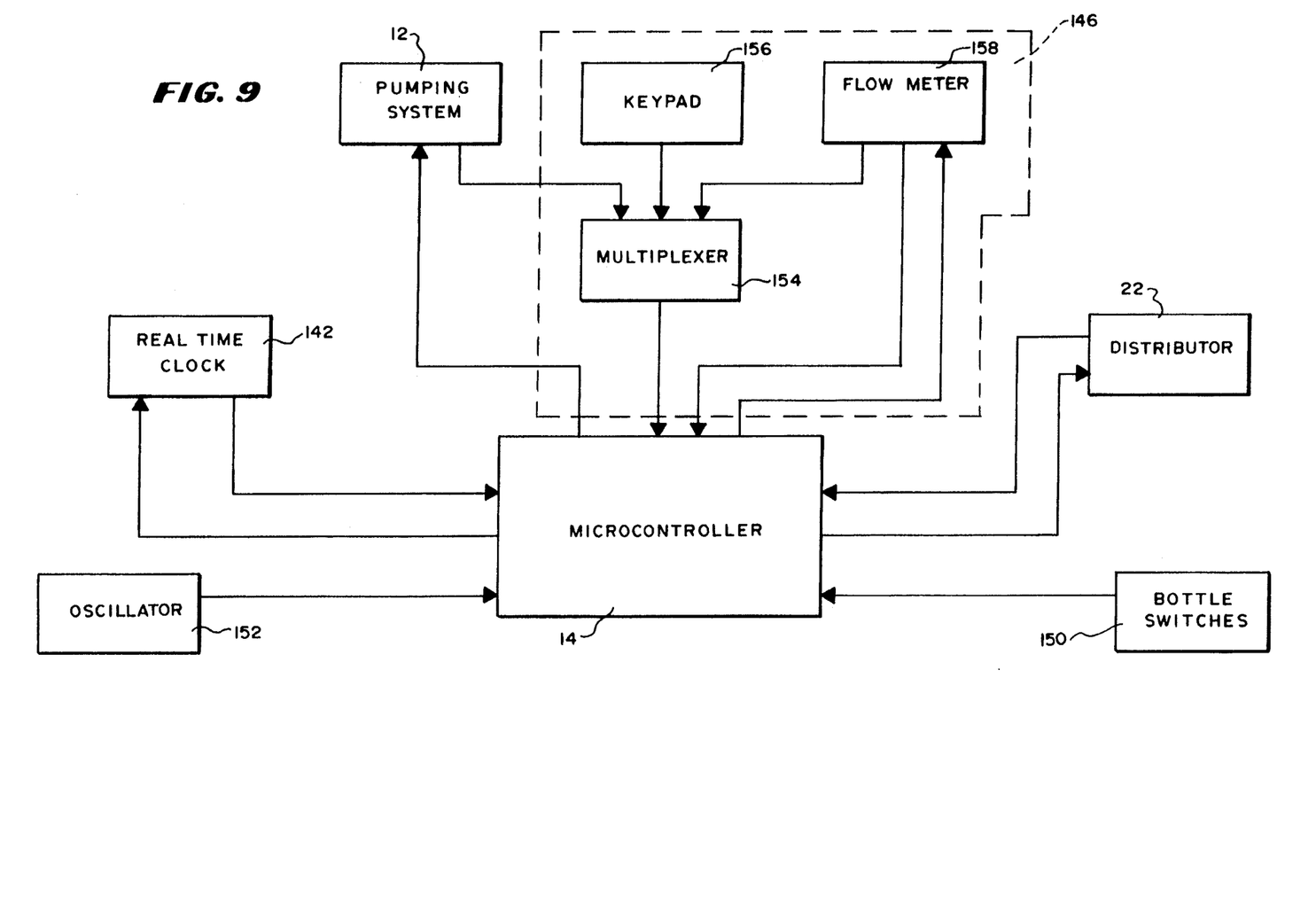
FIG. 9 is a block diagram of a control system for the sampler.

In FIG. 9, there is shown a block diagram of the microprocessor control system used in the preferred embodiment having the microcontroller 14, the pumping system 12, a real time clock 142, an input interface 146, a distributor 22 and a set of bottle switches 150. The microcontroller 14 is a Motorola MC68HC705C8P microcontroller sold by Motorola, Inc., Microprocessor Products Group, Microcontroller Division, Oak Hill, Tex., programmed in accordance with the software listing of attachment A to this specification.

To control the wastewater sampler, an external oscillator 152 is connected to the microcontroller 14 in a conventional manner to establish a basic clock rate. The microcontroller receives signals from the real time clock 142 and from the input interface 146 to which it is electrally connected. The real time clock 142 provides presetable periodic signals to the microcontroller 14. Their signals are used to time events such as the drawing of samples or the like. The real time clock 142 periodically applies signals to the microcontroller 14 and is powered by a seperate source of power such as a lithium battery which enables it to continue sending coded pulses that indicate the real time. It receives a signal from the microcontroller 14 upon initialization which sets the real time into the real time clock 142 so that it may provide accurate indications of time to the microcontroller.

The microcontroller 14, if it loses power, inquires of the real time clock 142 about the actual time upon receiving power to reset its registers. The real time clock also receives signals from the microcontroller 14 as to the duration of periodic intervals between signals to be sent by the real time clock 142 to the microprocessor 14 for timing events such as the drawing of samples or the like as preprogrammed into the microcontroller 14 through the user interface.

For programming and timing some events, the input interface 146 includes: (1) a flow-meter connector 158; and (2) a keypad 156 and a display that permits an operator to set the parameters such as the amount of flow between samples or the like. The flow meter connector may be electrically connected to a flow meter that provides a measure of wastewater flowing through the wastewater pipe that is being sampled. The signals from the flow meter may be utilized to cause a sample to be drawn at periodic intervals.

To prevent overflow of sample, the distributer 22 moves the outlet hose 32 between the first container 24A (FIG. 1) and 24B (FIG. 2) under the control of the microcontroller 14 when the microcontroller 14 determines that the container into which it is depositing samples is full from a calculation based on the number of samples and the volume of each sample. It may then cause the distributor to begin depositing samples into the other container. The microcontroller 14 may be programmed to make this change at any selected volume of sample.

The bottle switches 150 are lever actuated push button switches which sense the presence of a container 24A or 24B and apply the signal to the microcontroller 14 indicating the presence or absence of the container. With this arrangement, the microcontroller 14 senses the presence of at least one of the containers 24A and 24B before it begins actuating the pump to draw samples.

To control the pumping intervals, the microcontroller 14 may be programmed through the user interface to initiate pumping action from the pumping system 12 at intervals which occur after a predetermined amount of time or after a predetermined amount of flow as set through the user interface. The microcontroller 14 also has programmed into it the number of pumping cycles from the pumping system 12 for a continuous sample and the volume of the wastewater that is to be applied to the containers 24A or 24B (FIG. 1) before signaling the distributor 22 to move to a new container, provided the bottle switches 150 indicate that an empty container is in place.

The pumping system 12 is also connected to the user interface which contains a multiplexor and transmitts signals thereto indicating the number of pump cycles. These signals are applied to the microcontroller 14 to count the wastewater which has been drawn either as a sample or to be pumped upwardly to a fixed location and downwardly to clear the line.

To control the positioning of the outlet hose 32 by the distributor 22, the distributor 22 includes a right and left position switch, which in the preferred embodiment are optical switches. These switches are electrically connected to the microcontroller 14 to indicate the initial position of the outlet of the hose 32.

When the microcontroller senses that one of the containers 24A and 24B is full and the other container is empty and in place, it applies a signal to the distributor 22 which is driven into position over the empty container. At that position, the optical switch on that side is interrupted and sends a signal back to the microcontroller and the microcontroller stops movement of the distributor 22 in place. This cycle may be repeated an indefinate number of time assuming that the full containers 24A and 24B are removed and replaced by empty containers.

The user interface 146 includes a multiplex unit 154 which is electrically connected to a keypad 156, the flow meter connector 158 and an output conductor from the pumping system 12. It periodically scans these units and sends signals to the microprocessor indicating the amount of sample drawn by the pumping system 12 or input programming from the keypad or control signals from the keypad 156 or flow volume values from a flow meter connected to the flow meter connector 158. The flow meter connector 158 also receives; (1) event signals from the microcontroller 14 for marking a strip chart or the like connected to the flow meter or internal to the flow meter; and (2) signals from a seperate detector of wastewater in the pipe to signal the microcontroller 14 to indicate the presence of absence of flow through the wastewater pipe.

Figure 10:
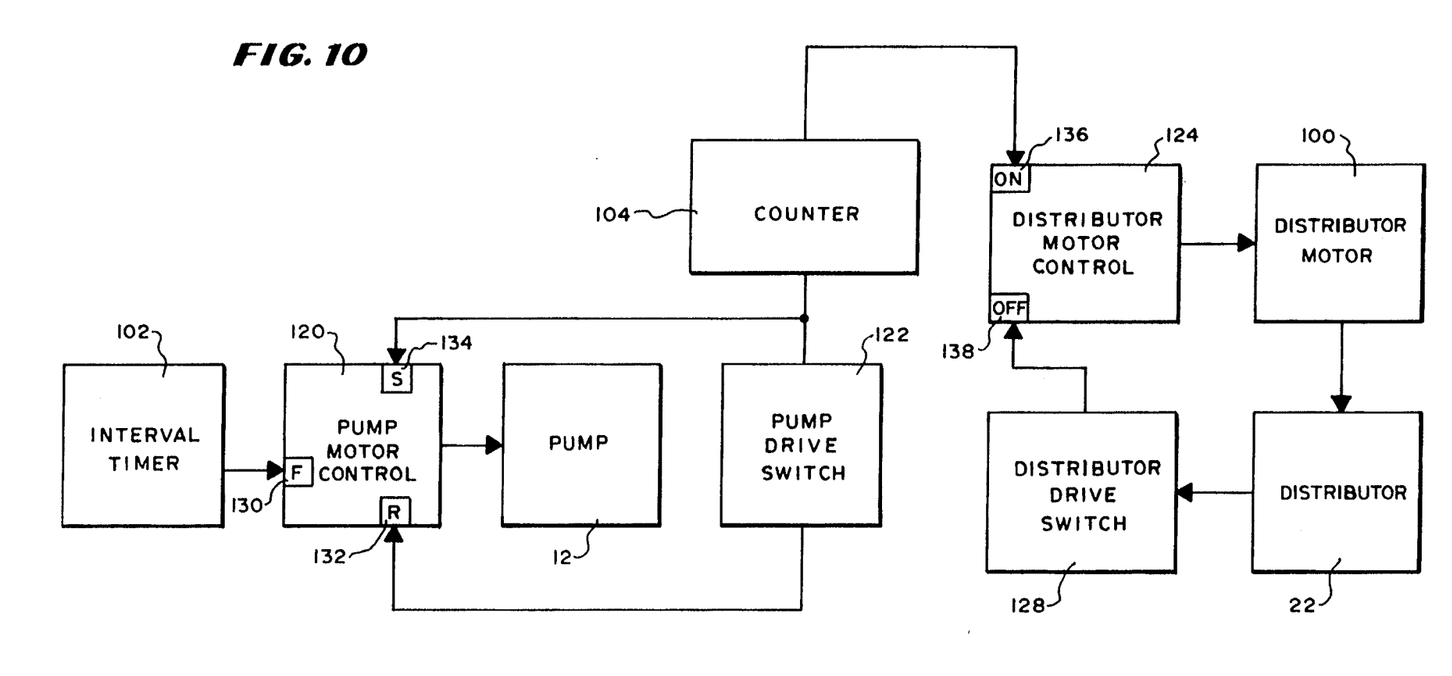
FIG. 10 is a schematic illustrative diagram of a hard wired version of the wastewater sampler.

In FIG. 10, there is shown a block diagram of a hardware control system which performs the functions which in the preferred embodiment are performed by the Motorola microcontroller model MC68HC705C8P used in the preferred embodiment and available from Motorola, Inc. Microprocessor Products Group, Microcontroller Division, Oak Hill, Tex., utilizing the software list of attachment A connected as shown by the block diagram of FIG. 9. The control system shown in FIG. 10 includes an interval timer 102, a ring counter 104, a pump motor control 120, the pump assembly 12, a pump drive switch 122, a distributor motor control 124, a distributor motor 100 and the distributor drive switch 128.

To start, stop and control the direction of rotation of the pump assembly 12, the pump motor control 120 includes a switching arrangement having: (1) a first position into which it is switched by a signal from the interval timer 102 to the forward drive terminal 130 of the pump motor control 120 and in which position it applies power to the pump assembly 12 in a direction that causes the pump assembly 12 to draw fluid into the intake hose 30 (FIG. 1); (2) a second position into which it is switched by a signal from the pump drive switch 122 to the reverse drive terminal 132 and in which position it stops the pump assembly 12 and applies power to the pump assembly 12 in a direction that causes the pump assembly 12 to force fluid out of the inlet of the intake hose 32 to clear the hose of fluid before another sample is taken; and (3) a third position into which it is switched by a signal from the pump drive switch 122 to the stop terminal 134 and in which position it stops the pump assembly 12. This signal is also applied to the adjustable ring counter 104 which has its selectable output terminal connected: (1) to the terminal 136 of the distributor motor control 124 for a purpose to be described hereinafter; and to its own reset terminal to permit another count cycle.

To generate the signals that are applied to the reverse input terminal 132, the stop terminal 134 and the counter 104 input terminal, the pump drive switch 122 includes a cam-operated revolution-sensing switch that is controlled by the rotation of the pump motor and a stepping switch that counts operations of the cam-operated revolution-sensing switch. The stepping switch produces a contact closure to provide a signal to the reverse input terminal 132 of the pump motor control 120 when the pump assembly 12 has rotated a predetermined number of revolutions in the forward direction to draw a certain volume of fluid into the intake hose 16 and then produces another contact closure which provides a signal to the stop input terminal 134 of the pump motor control 120 and to the on terminal 136 of the distributor motor control 124 when the pump has rotated a predetermined number of revolutions in the reverse direction to clear the intake hose 30.

The distributor motor control 124 includes a switching arrangement having an on position in which it applies power to the distributor motor 126 to rotate the distributor 22 into a position in which it is switched by a signal to its on terminal 136 from the counter 104. This counter 104 counts signals from the pump drive switch 122 indicating a predetermined number of samples have been drawn and applied to a container. The distributor motor control 124 is switched to its off position by a signal applied to its input terminal 138 in which position it stops the rotation of the distributor motor 126 to stop the distributor 22 with an outlet of the peristaltic pump hose 32 over the other container. To generate the signal that is applied to the off terminal 136 of the distributor motor control 124 the distributor drive switch 128, which may be a cam-operated switch, is positioned to be depressed each time the distributor 22 is rotated the distance between two successive containers.

With this arrangement, the interval timer 102 in the computer energizes the pump motor control 120 which energizes the pump assembly 12 to draw a sample as measured by the pump drive switch 122. At the end of drawing the sample, the pump drive switch 122 applies the signal to the counter 104 which resets the pump motor control 120 for the next interval and stops the pump motor by applying a signal to the control 134. This signal is also applied to the counter 104 which counts a predetermined number of counts and then applies a signal to the distributor motor control 124 indicating the container is full and initiating motion of the distributor motor to a predetermined position of the distributor 22 where it hits a switch and turns off the distributor motor by applying a signal to the off switch 138. The counter 104 is a setable ring counter which may be set to take a predetermined number of samples.

From the above description, it can be understood that the wastewater sampler of this invention has several advantages such as: (1) it is not easily clogged; (2) it provides a more accurate measure of the amount of solids in the wastewater; (3) it is relatively uncomplicated; (4) it is readily adaptable to scooping samples manually while at the same time permitting direct pumping for higher accuracy; and (5) it does not require continuous attendance and may fill sequentially composite containers automatically.

Although a specific embodiment has been described with some particularity, many modifications and variations may be made in this specific embodiment without deviating from the invention. Therefore, it is to be understood that, within the scope of the appended claims, the invention may be practiced other than as specifically described.

We claim:

1. A wastewater composite sampler comprising:
   a flow-through-chamber having an inlet port and an outlet port;
   said inlet port and outlet port being adapted to communicate with a wastewater pipe so that wastewater flows from the inlet port into the flow-through-chamber and into the outlet port back into the wastewater pipe;
   said flow-through-chamber being contoured to cause wastewater flowing from the inlet port to drop to a lower level;
   an intake nozzle having a longitudinal axis and a tip positioned with its tip located so that the wastewater falling to the lower level flows over at least a lower portion of the intake nozzle;
   the intake nozzle having a slight taper about its longitudinal axis and an intake opening at its tip shaped to cancel venturi forces; and
   means for pumping wastewater upwardly through the intake nozzle for collection.

2. A wastewater composite sampler in accordance with claim 1 in which the taper of the intake nozzle is between 1.5 and 3 degrees from its longitudinal axis, whereby the intake nozzel is self-cleaning.

3. A wastewater composite sampler in accordance with claim 2 in which said means for pumping wastewater through the intake nozzle is preset to pump wastewater upwardly at substantially the same flow rate as wastewater is flowing through said inlet port.

4. A wastewater composite sampler in accordance with claim 3 in which the means for pumping wastewater draws wastewater at a velocity of between 1 and 12 linear feet per second.

5. A wastewater composite sampler in accordance with claim 4 in which the intake nozzle is positioned at an angle to the flow of wastewater and has an intake port selected to cancel venturi effects.

6. A wastewater composite sampler in accordance with claim 5 further including:
   a distributor means;
   said distributor means communicating through said means for pumping wastewater with said intake nozzle;
   means for determining the number of samples drawn;
   means for determining the amount of each sample; and
   control means for moving said distributor means from one container to another when the amount of wastewater in each sample multiplied by the number of samples equals a predetermined volume.

7. A wastewater composite sampler in accordance with claim 6 in which said intake nozzle has a longitudinal axis, the inlet port of the flow-through-chamber has a longitudinal axis; the intake opening of the intake nozzle opens at an angle of between 5 degrees to 40 degrees with the longitudinal axis of the inlet port of the flow-through-chamber wherein a plane defining the plane of the inlet port of the flow-through-chamber is at an angle of between 5 degrees and 40 degrees with the vertical.

8. A wastewater composite sampler in accordance with claim 7 in which the flow-through-chamber includes a removable cover.

9. A wastewater composite sampler in accordance with claim 1 in which said means for pumping wastewater through the intake nozzle is preset to pump wastewater upwardly at substantially the same flow rate as wastewater is flowing through said inlet port.

10. A wastewater composite sampler in accordance with claim 9 in which the intake nozzle is positioned at an angle to the flow of wastewater and has an intake port selected to cancel venturi effects.

11. A wastewater composite sampler in accordance with claim 10 further including:
a distributor means;
said distributor means communicating through said means for pumping wastewater with said intake nozzle;
means for determining the number of samples drawn;
means for determining the amount of each sample; and
control means for moving said distributor means from one container to another when the amount of wastewater in each sample multiplied by the number of samples equals a predetermined volume.

12. A wastewater composite sampler in accordance with claim 11 in which the intake port of the intake nozzle opens at an angle of between 5 degrees to 40 degrees with the longitudinal axis of the inlet port of the flow-through-chamber.

13. A wastewater composite sampler in accordance with claim 1 in which the means for pumping wastewater draws wastewater at a velocity of between 1 and 12 linear feet per second.

14. A wastewater composite sampler in accordance with claim 13 in which the intake nozzle is positioned at an angle to the flow of wastewater and has an intake port selected to cancel venturi effects.

15. A wastewater sampler in accordance with claim 14 further including:
a distributor means;
said distributor means communicating through said means for pumping wastewater with said intake nozzle;
means for determining the number of samples drawn;
means for determining the amount of each sample; and
control means for moving said distributor means from one container to another when the amount of wastewater in each sample multiplied by the number of samples equals a predetermined volume.

16. A wastewater composite sampler in accordance with claim 15 in which the intake port of the intake nozzle opens at an angle of between 5 degrees to 40 degrees with the longitudinal axis of the inlet port of the flow-through-chamber.

17. A wastewater composite sampler in accordance with claim 1 in which the intake nozzle is positioned at an angle to the flow of wastewater and has an intake port selected to cancel venturi effects.

18. A wastewater composite sampler in accordance with claim 17 further including:
a distributor means;
said distributor means communicating through said means for pumping wastewater with said intake nozzle;
means for determining the number of samples drawn;
means for determining the amount of each sample; and
control means for moving said distributor means from one container to another when the amount of wastewater in each sample multiplied by the number of samples equals a predetermined volume.

19. A wastewater composite sampler in accordance with claim 18 in which the intake port of the intake nozzle opens at an angle of between 5 degrees to 40 degrees with the longitudinal axis of the inlet port of the flow-through-chamber.

20. A wastewater composite sampler in accordance with claim 1 further including:
a distributor means;
said distributor means communicating through said means for pumping wastewater with said intake nozzle;
means for determining the number of samples drawn;
means for determining the amount of each sample; and
control means for moving said distributor means from one container to another when the amount of wastewater in each sample multiplied by the number of samples equals a predetermined volume.

21. A wastewater composite sampler in accordance with claim 20 in which the intake port of the intake nozzle opens at an angle of between 5 degrees and 40 degrees with the longitudinal axis of the inlet port of the flow-through-chamber.

22. A wastewater composite sampler in accordance with claim 1 in which the intake port of the intake nozzle opens at an angle of between 5 degrees to 40 degrees with the longitudinal axis of the inlet port of the flow-through-chamber.

23. A method of assembling a wastewater sampler, comprising the steps of:
connecting a flow-through-chamber having an inlet port and an outlet port with said inlet port and outlet port communicating with a wastewater pipe so that wastewater flows from the inlet port into the flow-through-chamber and into the outlet port back into the wastewater pipe and said flow-through-chamber being contoured to cause wastewater flowing from the inlet port to drop to a lower level; and
mounting an intake nozzle positioned with its tip located so that the wastewater falling to the lower level flows over at least a lower portion of the intake nozzle; wherein the intake nozzle has a slight taper and an intake opening shaped to cancel venturi forces.

24. A method according to claim 23 in which the step of mounting the nozzle includes the step of sliding the nozzle into a holder, adjusting its position so that its intake port is centered near the center of the flow of wastewater and tightening the holder to hold the nozzle in place.

* * * * *